US010977485B2

(12) United States Patent
Wang et al.

(10) Patent No.: US 10,977,485 B2
(45) Date of Patent: Apr. 13, 2021

(54) METHOD FOR IDENTIFYING RT POSITIONING IMAGE, COMPUTER PROGRAM, AND COMPUTER STORAGE

(71) Applicant: General Electric Company, Schenectady, NY (US)

(72) Inventors: Xueli Wang, Beijing (CN); Hongyu Li, Beijing (CN); Weiwei Xing, Beijing (CN)

(73) Assignee: General Electric Company, Schenectady, NY (US)

(*) Notice: Subject to any disclaimer, the term of this patent is extended or adjusted under 35 U.S.C. 154(b) by 119 days.

(21) Appl. No.: 16/215,865

(22) Filed: Dec. 11, 2018

(65) Prior Publication Data
US 2019/0188461 A1   Jun. 20, 2019

(30) Foreign Application Priority Data

Dec. 14, 2017 (CN) .......................... 201711338889.4

(51) Int. Cl.
| | |
|---|---|
| *G06T 7/13* | (2017.01) |
| *G06K 9/00* | (2006.01) |
| *G06T 7/136* | (2017.01) |
| *G06T 5/30* | (2006.01) |
| *G06T 7/11* | (2017.01) |
| *A61N 5/10* | (2006.01) |

(52) U.S. Cl.
CPC ....... *G06K 9/00369* (2013.01); *A61N 5/1049* (2013.01); *G06T 5/30* (2013.01); *G06T 7/11* (2017.01); *G06T 7/13* (2017.01); *G06T 7/136* (2017.01); *A61N 2005/1061* (2013.01); *G06K 2209/05* (2013.01); *G06T 2207/10081* (2013.01); *G06T 2207/30004* (2013.01); *G06T 2207/30196* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,856,528 | A * | 8/1989 | Yang ........................ | G06T 7/62 382/131 |
| 6,031,929 | A * | 2/2000 | Maitz ...................... | G06T 7/168 382/132 |
| 6,775,399 | B1 * | 8/2004 | Jiang ........................ | G06T 5/30 382/128 |
| 8,078,255 | B2 * | 12/2011 | Bhandarkar .............. | G06T 7/35 600/407 |
| 10,665,003 | B2 * | 5/2020 | Polster ................. | A61B 6/5258 |
| 2003/0016851 | A1 * | 1/2003 | Kaufman ............... | A61B 6/032 382/131 |
| 2006/0228009 | A1 * | 10/2006 | Fidrich ..................... | G06T 7/12 382/128 |
| 2006/0228036 | A1 * | 10/2006 | Avinash .................. | G06T 5/003 382/254 |

(Continued)

*Primary Examiner* — Tsung Yin Tsai

(57) ABSTRACT

Embodiments of the present invention provide a method for processing a radiotherapy CT positioning image, comprising: defining a pixel having a CT value greater than or equal to a first threshold in an original CT image as a human body pixel; counting a number of human body pixels of each pixel row in the original CT image in an order from top to bottom; and determining a boundary of the human body according to the counting result.

8 Claims, 2 Drawing Sheets

(56) References Cited

U.S. PATENT DOCUMENTS

| | | | | |
|---|---|---|---|---|
| 2008/0061395 A1* | 3/2008 | Tkaczyk | ............... | G01T 1/2985 |
| | | | | 257/443 |
| 2008/0123924 A1* | 5/2008 | Nabatame | ............ | A61N 5/1049 |
| | | | | 382/131 |
| 2012/0059252 A1* | 3/2012 | Li | .......................... | A61B 6/032 |
| | | | | 600/425 |
| 2012/0184840 A1* | 7/2012 | Najarian | ............... | G06T 7/0012 |
| | | | | 600/408 |
| 2014/0328465 A1* | 11/2014 | Herrmann | ................. | G01T 1/17 |
| | | | | 378/62 |
| 2017/0020472 A1* | 1/2017 | Eusemann | ............ | A61B 6/463 |

* cited by examiner

METHOD FOR IDENTIFYING RT POSITIONING IMAGE, COMPUTER PROGRAM, AND COMPUTER STORAGE

FIELD OF THE INVENTION

The present invention relates to the medical imaging field, particularly to a method for processing a radiotherapy (RT) positioning CT image, computer program and computer storage medium.

BACKGROUND OF THE INVENTION

Before conducting an RT on a patient, a doctor may obtain a positioning image of the patent in advance by utilizing a CT (Computing Tomography) imaging apparatus and formulate an RT solution according to the positioning image.

When a CT positioning imaging is being performed, the patient sometimes needs to keep various specific postures, for example, with arms up, chest forward, and the like. Moreover, in addition to a bed board for supporting the patient, keeping these postures also need help from various different accessories, e.g., a head support for supporting a head, an arm support for supporting an arm, even a reticulate support membrane and the like that can be hardened and molded after accommodating a head.

When an RT is being performed, the patient needs to keep a position, a posture and the like that are consistent with those at the time of the CT positioning imaging, therefore, the bed board for supporting the patient can usually be compatible with a CT imaging apparatus and an RT apparatus simultaneously, and after the CT positioning imaging is finished, the bed board and the patient, accessories and the like thereon are transferred into the RT apparatus as they are, so as to ensure the above consistency.

Different from a traditional CT imaging method, during the CT imaging for RT positioning, since those specific postures are to be posed, the patient will usually go beyond a scanning field (an aperture of the CT imaging apparatus for RT positioning is typically larger than that of the traditional CT imaging apparatus as well) so that image data will be cut off. Subsequently, a special image processing is further needed to reconstruct the cut off portion of the image so as to ensure completeness of the image for the region of the patient to be performed RT, which at first needs to separate a human body image of the patient from the regions of the bed board, auxiliary accessories and the like, otherwise, the reconstructed human body image will have larger errors, seriously affecting the subsequent RT plan.

The prior art method is: removing the images of a supporting body under the bed board, of the bed board and of the accessories on the bed board from the image acquired by scanning in an order from the bottom to top. The manner for removing is to preset heights of these components in the image, then to remove the image data under the heights after acquiring the image, only with the portions above the heights kept as the human body image.

Even under a condition that the number of the accessories is small and the shapes of the accessories are simpler, it is still difficult to identify human body data using the above method. When the number of the accessories is increased and the shapes of the bed board or accessories are more complicated, it is more impossible. Therefore, the suppliers can only limit said function on a specific accessory and suggest the hospital not to use other accessories, which brings about difficulties to the actual RT work.

The person skilled in the art has been dedicated to studying more complicated algorithm to remove image data other than the human body as well, however, on one hand, the algorithm is too complicated, and on the other hand, the algorithm still needs to be adjusted directed to different accessories or bed board. In some cases, for example, CT value increasing due to changing of the materials for the accessories, inclined placement of accessories and the like, such method can still not accurately identify the human body in the image.

The above current situation results in disability of further reconstructing an accurate human body positioning image by methods such as interpolation and the like, thus unable to appropriately plan an RT solution.

Therefore, there is a need to provide a new method for processing an RT positioning CT image, such that no matter what kind of complicated environment (mainly including environments formed from a supporting bed of the patient, the auxiliary accessories and the like) the patient is in, the human body image of the patient can always be accurately identified.

BRIEF DESCRIPTION OF THE INVENTION

An objective of the present invention is to provide a method for processing an RT CT positioning image, which can accurately identify image data of human body in a CT original image.

Exemplary embodiments of the present invention provide a method for processing an RT CT positioning image, comprising: defining a pixel having a CT value greater than or equal to a first threshold in a CT original image as a human body pixel; counting a number of human body pixels of each pixel row in the original CT image in an order from top to bottom; and determining a boundary of the human body according to the counting result.

The exemplary embodiments of the present invention also provide a computer program used in an RT CT imaging system, configured to control the RT CT imaging system to carry out the above method for processing an RT CT positioning image.

The exemplary embodiments of the present invention further provide a computer storage for storing the computer program as mentioned above.

Other features and aspects will be apparent through the following detailed description, figures and claims.

BRIEF DESCRIPTION OF THE DRAWINGS

The present invention can be better understood in light of the description of exemplary embodiments of the present invention with reference to the accompanying drawings, in which.

DETAILED DESCRIPTION OF THE INVENTION

Figure 1:
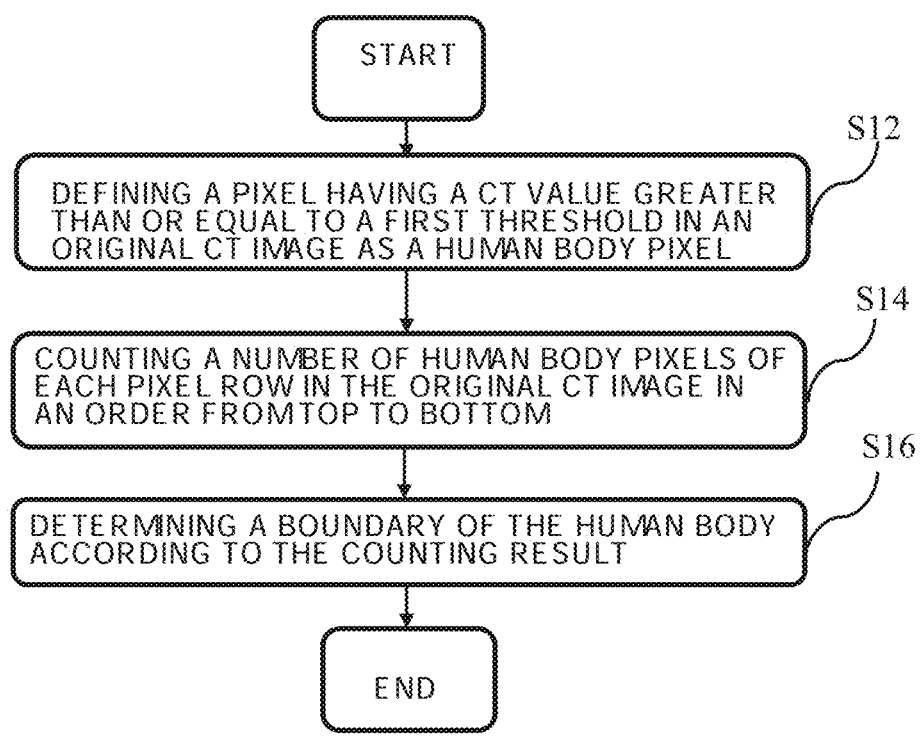
FIG. 1 is a flow chart of a method for processing an RT CT poisoning image provided by one embodiment of the present invention.

Hereafter, a detailed description will be given for preferred embodiments of the present disclosure. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical means in the art for one of ordinary skilled in the art associated with the contents disclosed in the present disclosure, which should not be regarded as insufficient disclosure of the present disclosure.

Unless defined otherwise, all the technical or scientific terms used in the Claims and the Description should have the same meanings as commonly understood by one of ordinary skilled in the art to which the present disclosure belongs. The terms "first", "second" and the like in the Description and the Claims of the present utility model do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, nor limited to being connected directly or indirectly.

The embodiments of the present invention may be used in an RT CT imaging system. In one embodiment, the RT CT imaging system may comprise a scanning system including a gantry. A cylindrical scanning chamber is formed on the gantry for accommodating a patient and a bed board for supporting the patient. Supporting accessories, e.g., head support, arm support and the like, are further placed on the bed board for keeping the patient to hold a fixed posture. A supporting body is provided under the bed board. A bulb and a detector are provided oppositely on the gantry. After penetrating a human body tissue, the accessories, the bed board and the supporting body in order, X-rays emitted by the bulb are received by the detector. The X-rays received by the detector are converted into digital image signals.

The RT CT imaging system further comprises a data collection system and an image reconstruction system. The data collection system is configured to collect the digital image signals and transmit them as raw CT image data to the image reconstruction system for image reconstruction. The raw CT image data contains human body image data and non-human body image data, so the reconstructed original CT image contains a human body image and a non-human body image. The image reconstruction system may be arranged on a computer and the obtained image by reconstruction may be displayed on a display connected to the computer. The obtained image by reconstruction consists of a plurality of pixels arranged in a form of digital matrix.

The RT CT imaging system further comprises a control system, which may also be arranged on the computer for controlling the scanning system, the data collection system and the image reconstruction system.

The method for processing an RT CT positioning image of the embodiments of the present invention is configured to process the original CT image so as to identify the human body image data therein more accurately. The above original CT image may be a CT image reconstructed according to the raw scanning data when RT positioning imaging is being performed. In order to reconstruct the human body data of the cut off portion in the original CT image, the existing human body image data therein needs to be identified for image reconstruction. Therefore, the less the non-human body image data of the components doped in the human body image data is, the more accurate the identifying result is.

Figure 2:
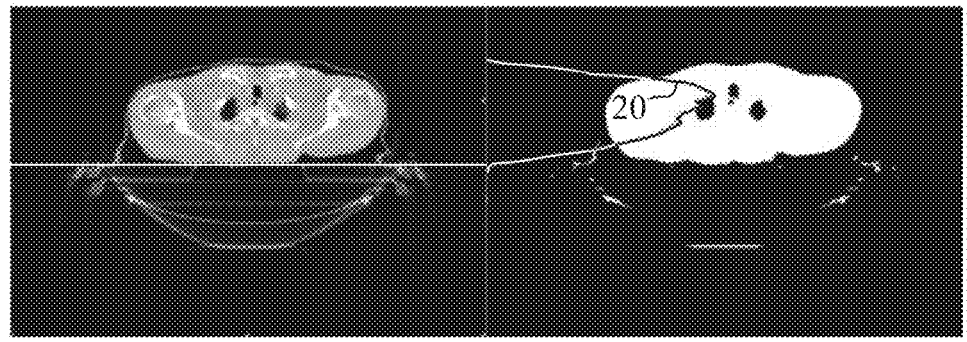
FIG. 2 is an exemplary figure in one embodiment of the present invention, in which an original CT image is binarized and human body pixels are identified.
Figure 3:
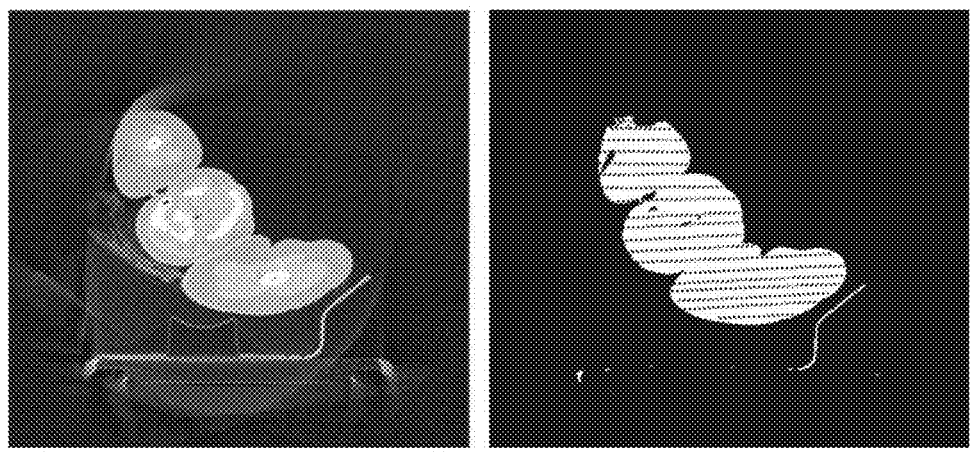
FIG. 3 is an exemplary figure in another embodiment of the present invention, in which the original CT image is binarized and human body pixels are identified.

FIG. 1 is a flow chart of a method for processing an RT CT poisoning image provided by one embodiment of the present invention, FIG. 2 is an exemplary figure in one embodiment of the present invention, in which an original CT image is binarized and human body pixels are identified, with the left of FIG. 2 being the original CT image and the right of FIG. 2 being the binarized image; FIG. 3 is an exemplary figure in another embodiment of the present invention, in which an original CT image is binarized and human body pixels are identified, with the left of FIG. 3 being the original CT image and the right of FIG. 3 being the binarized image.

As shown in FIG. 1, the method comprises steps S12, S14 and S16. In step S12, a pixel having a CT value greater than or equal to a first threshold in an original CT image is defined as a human body pixel. The first threshold is an empirical value for a human body CT value. Since the most parts of a human body consist of water, and the CT value of water is close to or equal to 0, the first threshold is set to be close to 0, for example, 200 HU, which can cover the CT values of the most parts of a human body.

Furthermore, in step S12, the human body pixels may be identified by a binarization method. For example, in the original CT image, a pixel value of a pixel having a CT value greater than or equal to the first threshold is defined as 1, and a pixel value of a pixel having a CT value less than the first threshold is defined as 0, resulting in the original CT image that has been binarized as shown in FIG. 2.

In step S14, a number of human body pixels of each pixel row in the original CT image is counted in an order from top to bottom.

It should be noted that the "from top to bottom" mentioned in the present application corresponds to the position relationships between the human body and its supporting components. For example, the human body is on the top, downward followed by the supporting accessories, the supporting bed board, the supporting body and the like in order. Therefore, in the original CT image, "top (up, on), bottom (down, under)" are defined according to such position relationships.

Taking FIG. 2 as an example, in step S14, further processing may be performed based on the binarized original CT image. In FIG. 2, a longitudinal coordinate of the image represents rows of the pixel matrix, and a horizontal coordinate of the image represents columns of the pixel matrix. Since the human body pixel has been defined in step S12, the number of the human body pixels for each row may be counted in order, and a boundary of the human body may be determined according to the counting result in step S16. The curve 20 in FIG. 2 represents a distribution of numbers of human body pixels on pixel rows.

In an application, the following conclusion may be obtained combining with specific shapes of human body, i.e., the number of the human body pixels of the row for the lower boundary is obviously less compared with the number of the pixels of the upper row thereof. Therefore, in step S16, the boundary of the human body may be determined by the following manner: judging whether the number of the human body pixels of the present pixel row decreases to a specific degree compared with the number of the human body pixels of the counted pixel rows, and identifying the present pixel row as a lower boundary of the human body if it does.

In order to quantify the specific degree, the embodiments of the present invention further put forward that during the process of counting from top to bottom, the pixel row with the greatest number of human body pixels may constantly be determined as a most-human-body-pixel-row according to the present counting result; then when continuing to count the number of the human body pixels of the present row, a ratio of the number of the human body pixels of the present row to the number of the human body pixels of the most-human-body-pixel-row is evaluated, and if the ratio of the number of the human body pixels of the present row to the number of the human body pixels of the most-human-body-pixel-row is less than or equal to a second threshold, the present pixel row is identified as the lower boundary of the human body, in which the second threshold may be, for example, 10%.

In the above way, the human body image may be accurately identified in the original CT image. For example, for the lung of the human body as shown in FIG. 2, the region thereof that has been imaged is an entirety. By further reconstructing the image of the cut off portion of the image of the lung of the human body according to the image data of the image of the lung, a more accurate and more complete image of the lung may be obtained.

As shown in FIG. 3, when the regions of the human body to be imaged comprise a plurality of independent body parts (e.g., comprising a head, a shoulder connected with each other), after the lower boundary is determined, it is still insufficient to determine the overall contour of the regions of the human body to be imaged, however, due to speciality of the human body structure, generally speaking, the regions to be imaged typically can only include a limited number (typically no more than 3) of body parts (e.g., head and two shoulders, or head and two lifting arms), therefore, based on such condition, the embodiments of the present invention put forward that the above method for processing an RT CT position image further comprises the following steps: recording a starting point, intermediate breakpoints and an ending point of the human body pixels for each pixel row, and identifying a contour formed by all the starting points, intermediate breakpoints and ending points as a human body part contour. In this way, all regions representing the body parts that are connected with each other or independent from each other may be obtained in the image.

For example, when human body pixels are counted for each pixel row from left to right, the first human body pixel is a starting point, the last human body pixel is an ending point, and all the intermediate ones adjacent to the non-human body points are intermediate points.

In order to remove noise brought by independent pixels or independent small regions, before further determining effective regions in the plurality of regions, the following operations may be performed: performing an erosion processing on the human body part contour, and performing a dilation processing on the erosion processed human body part contour. The above effective regions may be understood as body regions that actually need imaging detection, e.g., head, shoulder and the like.

Furthermore, determining effective regions may comprise a region division step, a human body pixel area calculation step and an effective region determination step. In the region division step, the human body part contour is divided into a plurality of regions according to a shape of the human body part contour, and when dividing, the division may be performed in accordance with a general boundary of each region constituting the human body part contour. In the human body pixel area calculation step, an area of the human body pixels for each region is calculated. In the effective region determination step, a region with the area of the human body pixels being greater than or equal to a third threshold is determined as an effective region, in which the third threshold may be an empirical value, e.g., an imaging area of a specific body part. In the effective region determination step, according to the number N of the body parts to be imaged, N regions with the greatest areas of the human body pixels in all the regions may also be used as effect regions.

Furthermore, calculating an area of the human body pixels for each region comprises a pixel number calculation step, a physical pixel area calculation step and an image area calculation step. In the pixel number calculation step, a number of the human body pixels for each region is calculated. For example, the points in the human body part contour in FIG. 3 just represent the human body pixels in the human body part contour. Since the number of the human body pixels for each pixel row has been counted out, it only needs to sum the numbers of the human body pixels in the pixel rows covered by each region. In the physical pixel area calculation step, a physical pixel area of a single human body pixel is calculated, which is a square of a quotient of the scanning field defined during imaging to the size of the reconstructed matrix. In the image area calculation step, by multiplying the results obtained by the above two steps with each other, an image area of each region can just be obtained, i.e., multiplying the number of the human body pixels for each region by the physical pixel area of a single human body pixel to obtain an image area for each region.

Through a train of thought totally opposite to the prior art, the embodiments of the present invention, in an original CT image, predefine a human body pixel according to a CT value, then count numbers of the human body pixels in the pixel rows from top to bottom. According to the numbers, human body image data may be accurately identified from the original CT image by combining some general experience of human body imaging, such that when reconstructing the cut off data subsequently, the input values are accurate, thus a more accurate and more complete human body image can be reconstructed. In addition, by identifying the human body image data in the order from top to bottom, restriction to the identifying function due to the shapes, materials, position status (e.g., inclining, coinciding with the human body part in heights) and the like of accessories, bed board and the like, is avoided. No matter what kind of complicated supporting environment a patient is in, an accurate identifying result can always be obtained.

The embodiments of the present invention also provide a computer program used in an RT CT imaging system, configured to control the RT CT imaging system to carry out the method for processing an RT CT positioning image of anyone of the above embodiments.

Specifically, the computer program may be installed on a computer system of the RT CT imaging system, configured to execute the following instructions: Instruction 1: defining a pixel having a CT value greater than or equal to a first threshold in an original CT image as a human body pixel; Instruction 2: counting a number of human body pixels of each pixel row in the original CT image in an order from top to bottom; Instruction 3: determining a boundary of the human body according to the counting result.

Specifically, in Instruction 1, in the original CT image, a pixel value of a pixel having a CT value greater than or equal to the first threshold is defined as 1, and a pixel value of a pixel having a CT value less than the first threshold is defined as 0.

Instruction 3 may comprise: judging whether the number of the human body pixels of the present pixel row decreases to a specific degree compared with the number of the human body pixels of the counted pixel rows, and identifying the present pixel row as a lower boundary of the human body if it does.

Specifically, Instruction 3 may comprise the following sub-instructions: Instruction 3-1: determining a pixel row with the greatest number of human body pixels as a most-human-body-pixel-row according to the present counting result; Instruction 3-2: if a ratio of the number of the human body pixels of the present pixel row to the number of the human body pixels of the most-human-body-pixel-row is less than or equal to a second threshold, identifying the present pixel row as the lower boundary of the human body.

The above computer program may further comprise Instruction 4: recording a starting point, intermediate breakpoints and an ending point of the human body pixels for each pixel row, and identifying a contour formed by all the starting points, intermediate breakpoints and ending points as a human body part contour.

The above computer program may further comprise Instruction 5, which includes the following sub-instructions: 5-1: performing erosion processing on the human body part contour; 5-2: performing a dilation processing on the erosion processed human body part contour.

The above computer program may further comprise Instruction 6, which includes the following sub-instructions: 6-1: dividing the human body part contour into a plurality of regions according to a shape of the human body part contour; 6-2: calculating an area of the human body pixels for each region; 6-3: determining a region having an area greater than or equal to a third threshold as an effective region.

Specifically, the sub-instruction 6-2 comprises the following sub-instructions: 6-2-1: calculating a number of the human body pixels for each region; 6-2-2: calculating a physical pixel area of a single human body pixel; 6-2-3: multiplying the number of the human body pixels for each region by the physical pixel area of a single human body pixel to obtain an image area for each region.

The embodiments of the present invention further provide a computer storage for storing the computer program as mentioned above.

Although some exemplary embodiments have been described as mentioned above, it should be understood that various modifications may still be made. For example, if the described techniques are carried out in different orders, and/or if the components in the described system, architecture, apparatus or circuit are combined in different ways and/or replaced or supplemented by additional components or equivalents thereof, proper results may still be achieved. Accordingly, other implementation also falls within a protection range of the claims.

We claim:

1. A method for processing a radiotherapy CT positioning image, comprising:
    defining a pixel having a CT value greater than or equal to a first threshold in an original CT image as a human body pixel;
    counting a number of human body pixels for each pixel row in the original CT image in an order from top to bottom; and
    determining a boundary of the human body according to the counting result.

2. The method of claim 1, wherein in the original CT image, a pixel value of a pixel having a CT value greater than or equal to the first threshold is defined as 1, and a pixel value of a pixel having a CT value less than the first threshold is defined as 0.

3. The method of claim 1, wherein the step of determining a boundary of the human body according to the counting result comprises:
    judging whether the number of the human body pixels of the present pixel row decreases to a specific degree compared with the number of the human body pixels of the counted pixel rows; and
    identifying the present pixel row as a lower boundary of the human body if it does.

4. The method of claim 3, wherein the step of determining a boundary of the human body according to the counting result comprises:
    determining a pixel row with the greatest number of human body pixels as a most-human-body-pixel-row according to the present counting result; and
    if a ratio of the number of the human body pixels of the present pixel row to the number of the human body pixels of the most-human-body-pixel-row is less than or equal to a second threshold, identifying the present pixel row as the lower boundary of the human body.

5. The method of claim 1, further comprising: recording a starting point, intermediate breakpoints and an ending point of the human body pixels for each pixel row, and identifying a contour formed by all the starting points, intermediate breakpoints and ending points as a human body part contour.

6. The method of claim 5, further comprising:
    performing an erosion processing on the human body part contour; and
    performing a dilation processing on the erosion processed human body part contour.

7. The method of claim 5, further comprising:
    dividing the human body part contour into a plurality of regions according to a shape of the human body part contour;
    calculating an area of the human body pixels for each region; and
    determining a region having an area greater than or equal to a third threshold as an effective region.

8. The method of claim 7, wherein the calculating an area of the human body pixels for each region comprises:
    calculating a number of the human body pixels for each region;
    calculating a physical pixel area of a single human body pixel; and
    multiplying the number of the human body pixels for each region by the physical pixel area of a single human body pixel to obtain an image area for each region.

* * * * *